US012806144B2

(12) United States Patent
Park et al.

(10) Patent No.: US 12,806,144 B2
(45) **Date of Patent: *Nov. 24, 2026**

(54) LIPIDS FOR DRUG DELIVERY, NANOPARTICLES COMPRISING SAME, AND COMPOSITION FOR DRUG DELIVERY COMPRISING NANOPARTICLES

(71) Applicant: SAMYANG HOLDINGS CORPORATION, Seoul (KR)

(72) Inventors: Jong Min Park, Seongnam-si (KR); Joung Pyo Nam, Seoul (KR); Hye Yeong Nam, Seongnam-si (KR); So Jin Lee, Seoul (KR); Kyu Jin Kyung, Yongin-si (KR); Yoo Jeong Yoon, Seongnam-si (KR)

(73) Assignee: SAMYANG HOLDINGS CORPORATION, Seoul (KR)

( * ) Notice: Subject to any disclaimer, the term of this patent is extended or adjusted under 35 U.S.C. 154(b) by 79 days.

This patent is subject to a terminal disclaimer.

(21) Appl. No.: 18/723,272

(22) PCT Filed: Dec. 23, 2022

(86) PCT No.: PCT/KR2022/021160
§ 371 (c)(1),
(2) Date: Jun. 21, 2024

(87) PCT Pub. No.: WO2023/121380
PCT Pub. Date: Jun. 29, 2023

(65) Prior Publication Data

US 2025/0057766 A1 Feb. 20, 2025

(30) Foreign Application Priority Data

Dec. 23, 2021 (KR) ........................ 10-2021-0185685

(51) Int. Cl.
*A61K 9/1271* (2025.01)
*A61K 9/51* (2006.01)
(Continued)

(52) U.S. Cl.
CPC .......... *A61K 9/1271* (2013.01); *A61K 9/5123* (2013.01); *A61K 9/5153* (2013.01); *C07C 231/14* (2013.01); *C07C 237/16* (2013.01)

(58) Field of Classification Search
CPC ................ A61K 9/1271; A61K 9/5123; A61K 9/5153; A61K 47/6929; A61K 47/543;
(Continued)

(56) References Cited

U.S. PATENT DOCUMENTS

| | | | | |
|---|---|---|---|---|
| 9,526,795 B2 * | 12/2016 | Van | .................... | A61K 31/4745 |
| 2011/0257253 A1 * | 10/2011 | Seo | ...................... | A61K 9/5192 514/772.1 |

(Continued)

FOREIGN PATENT DOCUMENTS

| | | |
|---|---|---|
| JP | 2012-521358 A | 9/2012 |
| KR | 2003-0032897 A | 4/2003 |

(Continued)

OTHER PUBLICATIONS

Gary et al., "Polymer-Based siRNA Delivery: Perspectives on the Fundamental and Phenomenological distinctions from Polymer-Based DNA Delivery," ScienceDirect, Journal of Controlled Release, Feb. 16, 2007 (published online May 26, 2007), pp. 64-73.

(Continued)

*Primary Examiner* — Ernst V Arnold
(74) *Attorney, Agent, or Firm* — Birch, Stewart, Kolasch & Birch, LLP

(57) ABSTRACT

The present invention relates to lipids for drug delivery, nanoparticles comprising same, and a composition for drug delivery comprising the nanoparticles. More specifically, the present invention relates to: lipids useful for drug delivery
(Continued)

[Example (2OA-PAMAM): Delivery to lung]

since the lipids can easily form a complex with an anionic drug due to a specific structure thereof, and the complex can be encapsulated inside nanoparticles formed by an amphiphilic block copolymer; nanoparticles comprising same; and a composition for drug delivery comprising the lipids and a composition for drug delivery comprising the nanoparticles.

7 Claims, 2 Drawing Sheets

(51) Int. Cl.

| | |
|---|---|
| ***A61K 47/18*** | (2017.01) |
| ***C07C 231/14*** | (2006.01) |
| ***C07C 237/16*** | (2006.01) |

(58) Field of Classification Search

CPC .... A61K 47/18; C07C 231/14; C07C 237/16; C07C 237/06

See application file for complete search history.

(56) References Cited

U.S. PATENT DOCUMENTS

| | | | |
|---|---|---|---|
| 2012/0009222 | A1 | 1/2012 | Nguyen et al. |
| 2016/0145610 | A1 | 5/2016 | Lu et al. |

FOREIGN PATENT DOCUMENTS

| | | | |
|---|---|---|---|
| KR | 10-2011-0077818 | A | 7/2011 |
| KR | 10-1129509 | B1 | 4/2012 |
| WO | WO 2010/108108 | A2 | 9/2010 |

OTHER PUBLICATIONS

Mahon et al., "A Combinatorial Approach to Determine Functional Group Effects on Lipidoid-Mediated siRNA Delivery," National institutes of Health, vol. 21, No. 8, Aug. 18, 2010, pp. 1448-1454.

Paula et al., "Hydrophobization and Bioconjugation for Enhanced siRNA Delivery and Targeting," Cold Spring Harbor Laboratory Press, vol. 13, No. 4, published on Feb. 28, 2007, pp. 431-458.

Yin et al., "Biocompatible, pH-Sensitive AB2 Miktoarm Polymer-Based Polymersomes: Preparation, Characterization, and Acidic pH-Activated Nanostructural Transformation," Journal of Materials Chemistry, Jun. 11, 2012 (published Jul. 27, 2012), pp. 19168-19178.

Wang et al., "A Combinatorial Library of Unsaturated Lipidoids for Efficient Intracellular Gene Delivery," ACS Synthetic Biology, vol. 1, 2012, pp. 403-407.

Extended European Search Report for European Application No. 22912013.4, dated Sep. 23, 2025.

* cited by examiner

[Figure 1]
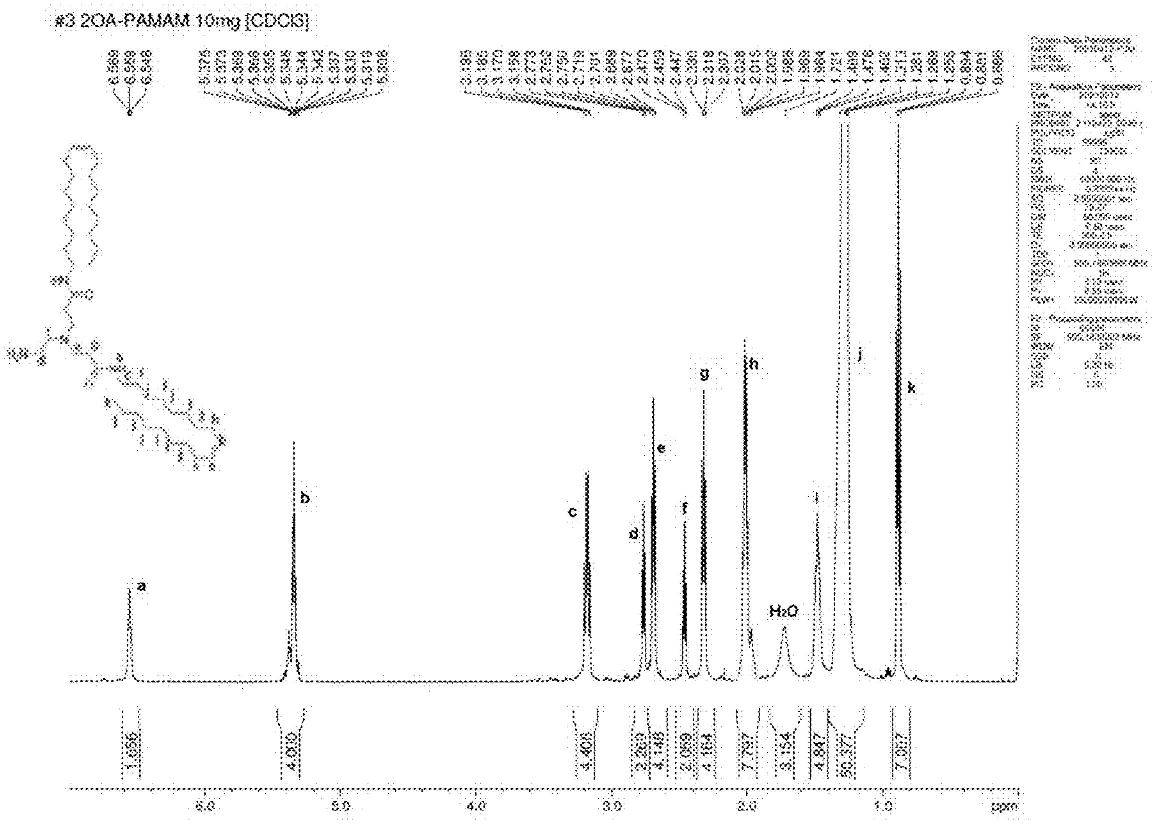
[Figure 2]
[Example (2OA-PAMAM): Delivery to lung]
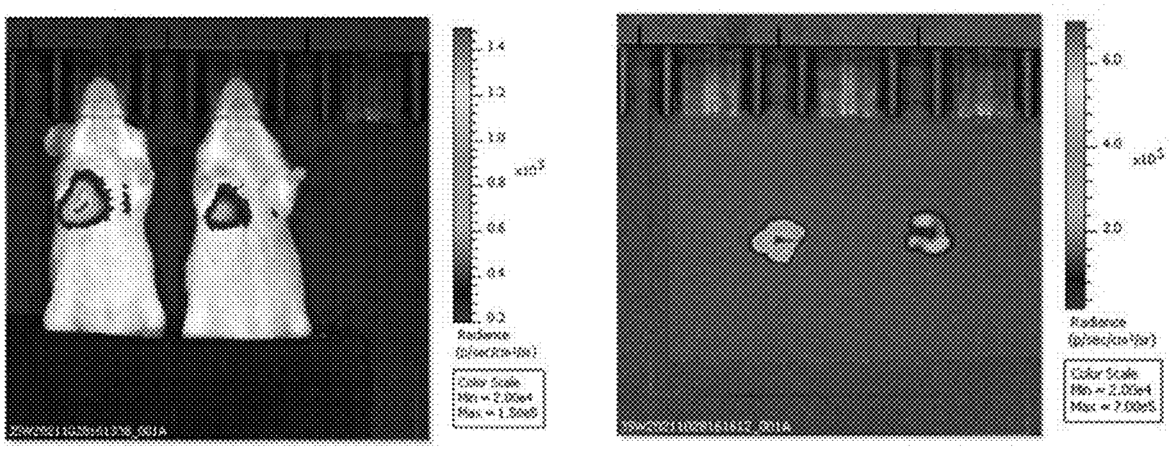

[Figure 3]
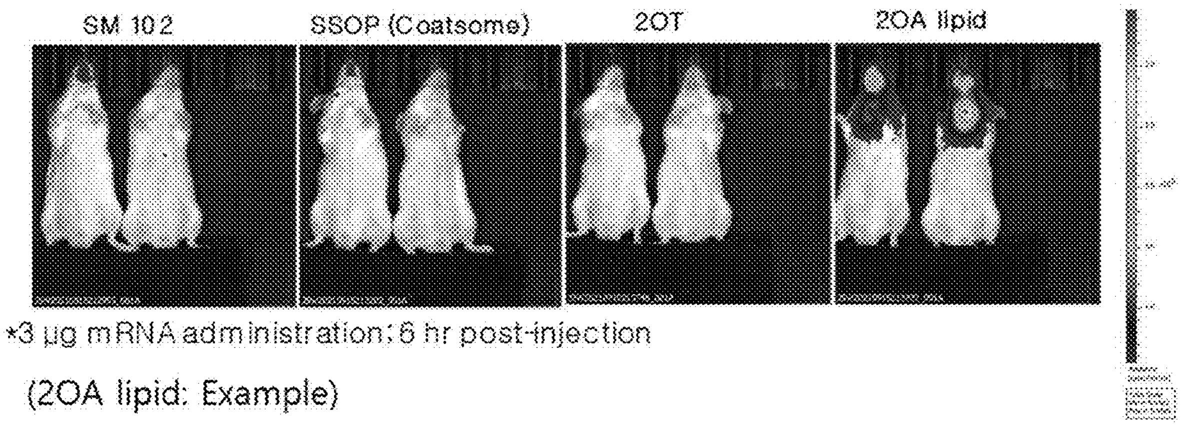

LIPIDS FOR DRUG DELIVERY, NANOPARTICLES COMPRISING SAME, AND COMPOSITION FOR DRUG DELIVERY COMPRISING NANOPARTICLES

TECHNICAL FIELD

The present invention relates to a lipid for drug delivery and nanoparticle comprising the same, and a composition for drug delivery comprising the nanoparticle, and more specifically, a lipid which can easily form a complex with anionic drug due to its specific structure and the complex can be encapsulated within nanoparticle formed by amphiphilic block copolymer and so is useful for drug delivery, and nanoparticle comprising the same, and a composition for drug delivery comprising the lipid and a composition for drug delivery comprising the nanoparticle.

BACKGROUND ART

In therapies using anionic drugs including nucleic acid, technologies for safe and efficient drug delivery have been researched for a long time, and various carriers and techniques for delivery have been developed. Carriers are mainly divided into viral carriers utilizing adenovirus, retrovirus or the like, and non-viral carriers utilizing cationic lipid, cationic polymer or the like. Viral carriers are known as being exposed to risks such as non-specific immune response, etc. and having many problems in commercialization due to the complexity of the production process. Thus, recent researches proceed in the direction to improve such disadvantages by using non-viral carriers. In comparison with viral carriers, non-viral carriers have advantages of fewer side effects in terms of in vivo safety, and lower production cost in terms of economy.

The representative non-viral carriers for delivering nucleic acid material are a complex of cationic lipid and nucleic acid (lipoplex) and a complex of polycationic polymer and nucleic acid (polyplex). Such a cationic lipid or polycationic polymer stabilizes anionic drug by forming a complex through electrostatic interaction with the anionic drug and increases intracellular delivery, and for these reasons, various researches thereof have been conducted (De Paula D, Bentley MV, Mahato RI, Hydrophobization and bioconjugation for enhanced siRNA delivery and targeting, RNA 13 (2007) 431-56; Gary D J, Puri N, Won Y Y, Polymer-based siRNA delivery: Perspectives on the fundamental and phenomenological distinctions from polymer-based DNA delivery, J Control release 121 (2007) 64-73).

In order to provide a mixed polymer nanoparticle composition capable of solubilizing a large amount of poorly water-soluble drug and having good stability in aqueous solution, Korean Laid-open Patent Publication No. 10-2003-0032897 discloses a mixed polymer nanoparticle composition which comprises an amphiphilic block copolymer of a hydrophilic block and a hydrophobic block, and a polylactic acid derivative containing carboxyl acid terminal group, and can form polymeric nanoparticles in body fluid or aqueous solution, and a pharmaceutical composition comprising polymeric nanoparticles formed by the mixed polymer nanoparticle composition within which a poorly water-soluble drug is contained.

CONTENTS OF THE INVENTION

Problems to be Solved

The purpose of the present invention is to provide a lipid which can easily form a complex with anionic drug due to its specific structure and the complex can be encapsulated within nanoparticle formed by amphiphilic block copolymer and so is useful for drug delivery, and nanoparticle comprising the same, and a composition for drug delivery comprising the lipid and a composition for drug delivery comprising the nanoparticle.

TECHNICAL MEANS

To achieve the above purpose, the first aspect of the present invention provides a lipid having a structure represented by the following formula 1:

[Formula 1]

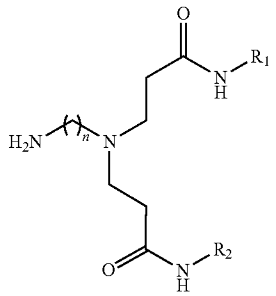

wherein, in the above formula 1, n is an integer of from 1 to 6, and each of $R_1$ and $R_2$ is independently selected from the group consisting of unsaturated hydrocarbon groups having 12 to 26 carbon atoms.

In an embodiment, in the above formula 1, n may be an integer of from 2 to 4.

In an embodiment, in the above formula 1, each of $R_1$ and $R_2$ may be independently —($C_5$-$C_{12}$alkylene)-CH═CH—($C_5$-$C_{12}$ alkyl).

More concretely, in the above formula 1, each of $R_1$ and $R_2$ may be independently —($C_6$-$C_{10}$ alkylene)-CH═CH—($C_6$-$C_{10}$ alkyl).

Still more concretely, in the above formula 1, $R_1$ and $R_2$ may be $—(CH_2)_8CH═CH(CH_2)_7CH_3$.

Still more concretely, the lipid may have the following structure:

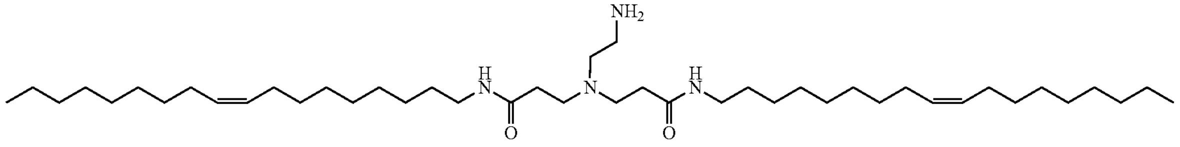 [SMILES: CCCCCCCC/C=C\CCCCCCCCNC(=O)CCN(CCN)CCC(=O)NCCCCCCCC/C=C\CCCCCCCC]

The second aspect of the present invention provides a method for preparing a lipid having a structure represented by the above formula 1, comprising the steps of: (1) reacting a compound of the following formula a with methyl acrylate to obtain a compound of the following formula b; (2) reacting a compound of the following formula b with a compound of the following formula c-1, or sequentially reacting with a compound of the following formula c-1 and a compound of the formula c-2, to obtain a compound of the following formula d-1 or d-2, respectively; and (3) deprotecting the compound of formula d-1 or d-2:

[Formula a]

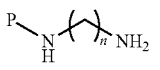

[Formula b]

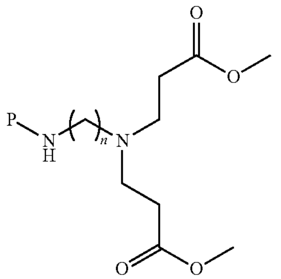

[Formula c-1]

$R_1$—$NH_2$

[Formula c-2]

$R_2$—$NH_2$

[Formula d-1]

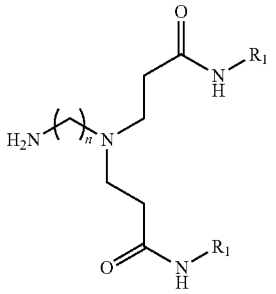

[Formula d-1]

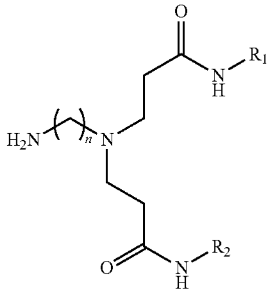

wherein

P is a protecting group, n is an integer of from 1 to 6, and each of $R_1$ and $R_2$ is independently selected from the group consisting of unsaturated hydrocarbon groups having 12 to 26 carbon atoms.

The third aspect of the present invention provides a composition for drug delivery comprising the lipid of the present invention.

The fourth aspect of the present invention provides drug-containing nanoparticle comprising: drug as effective ingredient; amphiphilic block copolymer; and the lipid of the present invention, wherein the drug and the lipid form a complex, and the complex is encapsulated within nanoparticle structure formed by the amphiphilic block copolymer.

In an embodiment, the drug-containing nanoparticle further comprises salt of polylactic acid, and the complex can be encapsulated within nanoparticle structure formed by the amphiphilic block copolymer and the salt of polylactic acid.

The fifth aspect of the present invention provides a composition for drug delivery comprising the drug-containing nanoparticle of the present invention.

Effect of the Invention

The lipid with a specific structure according to the present invention can easily form a complex with anionic drug and the complex can be effectively encapsulated within nanoparticle formed by amphiphilic block copolymer, and so a composition comprising the lipid, drug-containing nanoparticle prepared by utilizing the lipid and a composition comprising the nanoparticle can efficiently deliver a drug into the targeted living tissue.

BRIEF EXPLANATION OF THE DRAWINGS

FIG. 1 is NMR data of the lipid [2OA-PAMAM: (3-((2-aminoethyl)(3-(((Z)-nonadec-10-en-1-yl)amino)-3-oxopropyl)amino)-N-((Z)-octadec-9-en-1-yl)propanamide)] prepared in the example of the present invention.

FIG. 2 shows the results of a drug delivery experiment performed in Test Example 1 of the present invention and photographs of the results measured using a luminescence measurement imaging system.

FIG. 3 shows the results of a drug delivery experiment performed in Test Example 2 of the present invention and photographs of the results measured using a luminescence measurement imaging system.

CONCRETE MODE FOR CARRYING OUT THE INVENTION

The present invention will be explained in detail below.

A lipid provided by the first aspect of the present invention has a structure represented by the following formula 1:

[Formula 1]

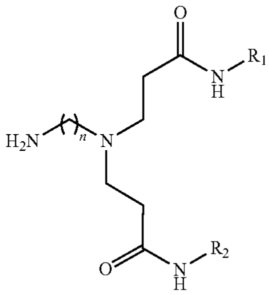

In the above formula 1, n is an integer of from 1 to 6, and more concretely, an integer of from 2 to 6, and each of $R_1$ and $R_2$ is independently selected from the group consisting of unsaturated hydrocarbon groups having 12 to 26 carbon atoms, and more concretely, the group consisting of unsaturated hydrocarbon groups having 14 to 22 carbon atoms, and still more concretely, the group consisting of unsaturated hydrocarbon groups having 16 to 20 carbon atoms.

In an embodiment, in the above formula 1, n may be an integer of from 2 to 4.

In an embodiment, in the above formula 1, each of $R_1$ and $R_2$ may be independently —($C_5$-$C_{12}$ alkylene)-CH═CH—($C_5$-$C_{12}$ alkyl).

More concretely, in the above formula 1, each of $R_1$ and $R_2$ may be independently —($C_6$-$C_{10}$ alkylene)-CH═CH—($C_6$-$C_{10}$ alkyl).

The "alkylene" and "alkyl" may be independently unsubstituted or substituted, and at this time the substituent may be, for example, hydroxyl group, halogen group or $C_1$-$C_4$ alkyl group, etc., but it is not limited thereto.

Still more concretely, in the above formula 1, $R_1$ and $R_2$ may be —$(CH_2)_8CH═CH(CH_2)_7CH_3$.

Still more concretely, the lipid may have the following structure:

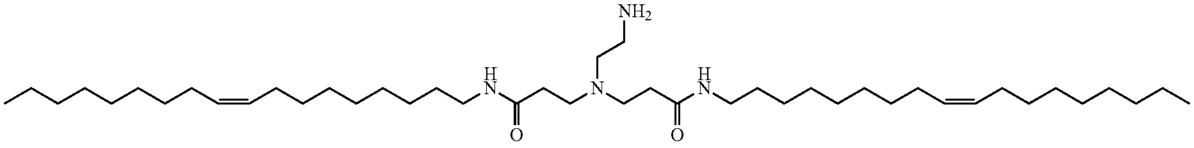 [SMILES: CCCCCCCC/C=C\CCCCCCCCNC(=O)CCN(CCN)CCC(=O)NCCCCCCCC/C=C\CCCCCCCC]

The second aspect of the present invention provides a method for preparing a lipid having a structure represented by the above formula 1, and the method comprises the steps of: (1) reacting a compound of the following formula a with methyl acrylate to obtain a compound of the following formula b; (2) reacting a compound of the following formula b with a compound of the following formula c-1, or sequentially reacting with a compound of the following formula c-1 and a compound of the formula c-2, to obtain a compound of the following formula d-1 or d-2, respectively; and (3) deprotecting the compound of formula d-1 or d-2:

[Formula a]

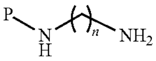

[Formula b]

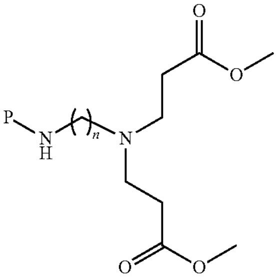

[Formula c-1]

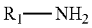

[Formula c-2]

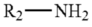

-continued

[Formula d-1]

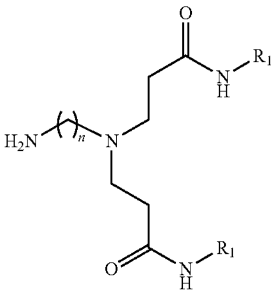

[Formula d-2]

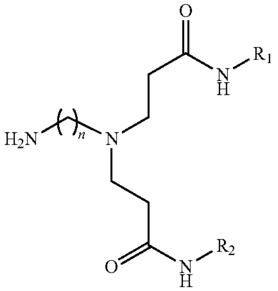

In the above formulas,

P is a protecting group, and more concretely, t-butoxycarbonyl group (t-BOC), and n, $R_1$ and $R_2$ are the same as defined in the above formula 1.

The overall synthesis scheme of the method for preparing the lipid of the present invention is illustratively shown as follows:

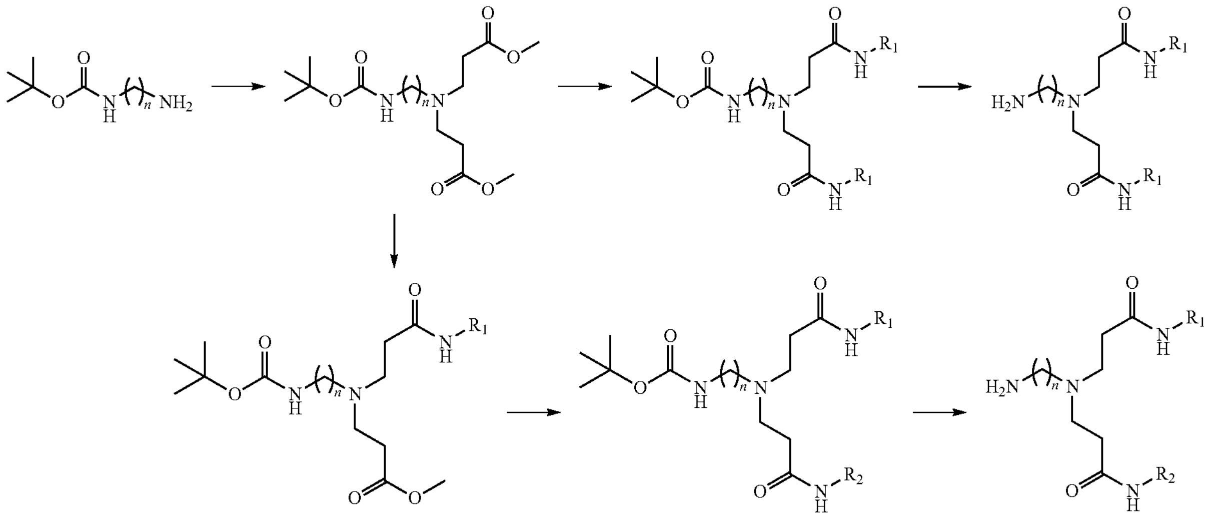

The third aspect of the present invention provides a composition for drug delivery comprising the lipid of the present invention.

The fourth aspect of the present invention provides drug-containing nanoparticle comprising: drug as effective ingredient; amphiphilic block copolymer; and the lipid of the present invention, wherein the drug and the lipid form a complex, and the complex is encapsulated within nanoparticle structure formed by the amphiphilic block copolymer.

In an embodiment, the drug-containing nanoparticle further comprises salt of polylactic acid, and the complex can be encapsulated within nanoparticle structure formed by the amphiphilic block copolymer and the salt of polylactic acid.

Also, the fifth aspect of the present invention provides a composition for drug delivery comprising the drug-containing nanoparticle of the present invention.

In the nanoparticle, in an aqueous environment, the hydrophilic part of the amphiphilic block copolymer forms an outer wall of the nanoparticle and the hydrophobic part of the amphiphilic block copolymer (together with the salt of polylactic acid if it is further contained) forms an inner wall of the nanoparticle, and inside the nanoparticle formed as such, the complex of the drug and the lipid of the present invention can be encapsulated. Such a nanoparticle structure enhances the stability of the effective ingredient in blood or body fluid.

In an embodiment, the drug may be selected from nucleic acid, polypeptide, virus or combination thereof.

The "nucleic acid" may be, for example, DNA, RNA, siRNA, shRNA, miRNA, mRNA, aptamer, antisense oligonucleotide, or a combination thereof, but it is not limited thereto.

The "polypeptide" may mean a protein having activity in the body such as antibody or fragment thereof, cytokine, hormone or analog thereof, or a protein that can be recognized as antigen through a series of processes in the body, including polypeptide sequence of antigen, analog or precursor thereof.

In an embodiment, the particle size of the nanoparticle can be defined by Z-average value, and for example, it may be 800 nm or less, 600 nm or less, 500 nm or less, 400 nm or less, 300 nm or less, 200 nm or less, or 150 nm or less, and also may be 10 nm or more, 50 nm or more, or 100 nm or more. In a concrete embodiment, the particle size of the nanoparticle defined by Z-average value may be, for example, 10 to 800 nm, 20 to 600 nm, 30 to 500 nm, 50 to 400 nm, or 80 to 300 nm.

The "Z-average" may mean the average of hydrodynamic diameter of particle distribution measured by using Dynamic light scattering (DSL). The nanoparticles have monodisperse particle distribution, and the polydispersity index thereof may be, for example, 0.01 to 0.50, 0.05 to 0.455, or 0.1 to 0.40.

Also, in an embodiment, the surface charge of the nanoparticle may be, for example, 0 mV or more, 1 mV or more, 5 mV or more, or 10 mV or more, and also may be 80 mV or less, 70 mV or less, or 60 mV or less. In a concrete embodiment, the surface charge of the nanoparticle may be, for example, 0 to 80 mV, 1 to 70 mV, or 5 to 60 mV. The surface charge may be measured in an environment close to biological environment, and for example, it may be measured in 8 to 12 mM HEPES buffer (pH 7.0 to 7.5).

In case of maintaining the particle size and surface charge of the nanoparticle to the above level, it is preferable in terms of stability of nanoparticle structure, amounts of the components and absorbability in the body, and easiness of sterilization as a pharmaceutical composition. For example, in case where the effective ingredient is nucleic acid, the one or more ends of the nucleic acid may be modified with one or more selected from the group consisting of cholesterol, tocopherol and fatty acids having 10 to 24 carbon atoms. The cholesterol, tocopherol and fatty acids having 10 to 24 carbon atoms include each analogue, derivative and metabolite of the cholesterol, tocopherol and fatty acids.

In an embodiment, if the effective ingredient is RNA, the amount of the effective ingredient may be, based on the total weight of the nanoparticle, for example, 0.05 to 30% by weight, 0.1 to 25% by weight, 0.25 to 20% by weight, 0.5 to 15% by weight, 1 to 10% by weight, or 1 to 5% by weight. If the amount of the effective ingredient is less than the above range, the amount of delivery carrier becomes too much as compared with the drug, and thus there may be a side effect due to the delivery carrier. If the amount of the effective ingredient is greater than the above range, the size of the nanoparticle becomes too large, and thus the nanoparticle stability may be lowered and the rate of loss during filter sterilization may increase.

In an embodiment, the amount of the lipid may be, based on 1 part by weight of the effective ingredient, for example, 500 parts by weight or less, 400 parts by weight or less, 300 parts by weight or less, 200 parts by weight or less, 100 parts by weight or less, 80 parts by weight or less, or 60 parts by weight or less, and it also may be 1 part by weight or more, 2 parts by weight or more, 3 parts by weight or more, 4 parts by weight or more, or 5 parts by weight or more. In an embodiment, the amount of the lipid may be, based on 1 part by weight of the effective ingredient, 1 to 500 parts by weight, 2 to 400 parts by weight, 3 to 300 parts by weight, 4 to 200 parts by weight, or 5 to 80 parts by weight. If the amount of the lipid is less than the above range, it may not form a stable complex with the effective ingredient. If the amount of the lipid is greater than the above range, the size of the nanoparticle becomes too large, and thus the nanoparticle stability may be lowered and the rate of loss during filter sterilization may increase.

In case where the effective ingredient is nucleic acid, the lipid and the nucleic acid are combined together through electrostatic interaction to form a complex. In an embodiment, the ratio of quantities of electric charge of the lipid (N) and the nucleic acid (P) (N/P: the ratio of the positive electric charge of the lipid to the negative electric charge of the nucleic acid) may be 0.5 or more, 1 or more, 2 or more, or 5 or more, and it also may be 200 or less, 150 or less, 100 or less, or 60 or less, and for example, it may be 0.5 to 200, 1 to 150, 2 to 100, or 5 to 60. If the ratio (N/P) is less than the above range, it may be difficult to form a complex containing a sufficient amount of the nucleic acid. In contrast, if the ratio (N/P) is greater than the above range, toxicity may be induced. In addition, the N/P ratio may act importantly for expression of the effective ingredient specifically in spleen.

In a concrete embodiment, the amphiphilic block copolymer may be an A-B type block copolymer comprising a hydrophilic A block and a hydrophobic B block. In an aqueous environment, the A-B type block copolymer forms core-shell type polymer nanoparticle wherein the hydrophobic B block forms the core (inner wall) and the hydrophilic A block forms the shell (outer wall).

In an embodiment, the hydrophilic A block may be one or more selected from the group consisting of polyalkylene glycol, polyvinyl alcohol, polyvinyl pyrrolidone, polyacrylamide, and derivatives thereof.

More concretely, the hydrophilic A block may be one or more selected from the group consisting of monomethoxypolyethylene glycol (mPEG), monoacetoxypolyethylene glycol, polyethylene glycol, copolymer of polyethylene and propylene glycol, and polyvinylpyrrolidone.

In an embodiment, the number average molecular weight (g/mol) of the hydrophilic A block may be 200 or more, 500 or more, 1,000 or more, or 2,000 or more, and it also may be 50,000 or less, 20,000 or less, 10,000 or less, or 5,000 or less, but it is not limited thereto.

Also, if necessary, the end of the hydrophilic A block may be chemically combined with a functional group or ligand capable of reaching specific tissue or cell, or a functional group capable of promoting intracellular delivery, in order to control in vivo distribution of polymer nanoparticle carrier formed by the amphiphilic block copolymer and salt of polylactic acid or to increase the efficiency of delivering the nanoparticle carrier into cell. In an embodiment, the functional group or ligand may be one or more selected from the group consisting of monosaccharides, polysaccharides, vitamins, peptides, proteins, and antibodies to cell surface receptors. More concretely, the functional group or ligand may be one or more selected from the group consisting of anisamide, vitamin B9 (folic acid), vitamin B12, vitamin A, galactose, lactose, mannose, hyaluronic acid, RGD peptide, NGR peptide, transferrin, antibody to transferrin receptor, etc.

The hydrophobic B block is a biocompatible, biodegradable polymer, and in an embodiment, it may be one or more selected from the group consisting of polyester, polyanhydride, polyamino acid, polyorthoester and polyphosphazine.

More concretely, the hydrophobic B block may be one or more selected from the group consisting of polylactide (PLA), polyglycolide, polycaprolactone, polydioxan-2-one, copolymer of polylactide and glycolide, copolymer of polylactide and polydioxan-2-one, copolymer of polylactide and polycaprolactone, and a copolymer of polyglycolide and polycaprolactone.

In an embodiment, the number average molecular weight (g/mol) of the hydrophobic B block may be 200 or more, 500 or more, 1,000 or more, or 1,700 or more, and it also may be 50,000 or less, 20,000 or less, 10,000 or less, or 6,000 or less, but it is not limited thereto.

For example, the number average molecular weight combination of the hydrophilic A block-hydrophobic B block may be 2,000-6,000, 2,000-4,000, 2,000-3,000, 2,000-1,700, etc., but it is not limited thereto.

Also, in an embodiment, in order to increase the hydrophobicity of and thereby improve the stability of the nanoparticle, the hydrophobic B block may be modified by chemically combining the hydroxyl group at the end of the hydrophobic B block with tocopherol, cholesterol, or fatty acid having 10 to 24 carbons.

In an embodiment, the salt of polylactic acid is distributed in the core (inner wall) of the nanoparticle, and acts to stabilize the nanoparticle by strengthening the hydrophobicity of the core, and at the same time, to effectively avoid reticuloendothelial system (RES) in the body. That is, the carboxylic anion in the salt of polylactic acid binds to the cationic complex more efficiently than polylactic acid, and decreases the surface potential of the polymer nanoparticle. Thereby, positive charge of the surface potential of the polymer nanoparticle becomes less than that of a polymer nanoparticle which does not contain a salt of polylactic acid, and thus it may be less captured by reticuloendothelial system and efficiently delivered to target sites (e.g., cancer cells, inflammatory cells, etc.).

In an embodiment, the number average molecular weight (g/mol) of the salt of polylactic acid may be 500 to 50,000, and more concretely, 1,000 to 10,000. If the number average molecular weight of the salt of polylactic acid is less than 500, the hydrophobicity becomes too low and thus it may not exist in the core (inner wall) of the nanoparticle, and if the number average molecular weight of the salt of polylactic acid is greater than 50,000, the size of the polymer nanoparticle may become too large.

In an embodiment, the end of the salt of polylactic acid (e.g., sodium salt of polylactic acid) opposite to the end of carboxylic acid-metal (e.g., carboxylic acid-sodium) may be substituted with one selected from the group consisting of hydroxyl, acetoxy, benzoyloxy, decanoyloxy, palmitoyloxy, and alkoxy having 1 to 2 carbon atoms.

In an embodiment, the salt of polylactic acid may be one or more selected from the group consisting of the compounds of the following Formulas 2 to 7 (wherein "COO" means carboxylic group, i.e., "C(═O)O"):

[Formula 2]

$$RO—CHZ—[A]_n—[B]_m—COOM$$

In Formula 2 above, A is —COO—CHZ—; B is —COO—CHY—, —COO—$CH_2CH_2CH_2CH_2CH_2$— or —COO—$CH_2CH_2OCH_2$—; R is hydrogen atom, or acetyl, benzoyl, decanoyl, palmitoyl, methyl or ethyl; each of Z and Y is hydrogen atom, or methyl or phenyl; M is Na, K or Li; n is an integer of from I to 30; and m is an integer of from 0 to 20.

[Formula 3]

$$RO—CHZ—[COO—CHX]_p—[COO—CHY']_q—COO—CHZ—COOM$$

In Formula 3 above, X is methyl; Y' is hydrogen atom or phenyl; p is an integer of from 0 to 25, q is an integer of from 0 to 25, with the proviso that p+q is an integer of from 5 to 25; R is hydrogen atom, or acetyl, benzoyl, decanoyl, palmitoyl, methyl or ethyl; M is Na, K or Li; and Z is hydrogen atom, methyl or phenyl.

[Formula 4]

$$RO—PAD—COO—W—M'$$

In Formula 4 above, W-M' is

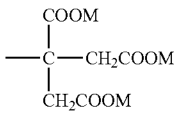

or

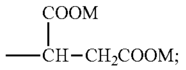

PAD is selected from the group consisting of D,L-polylactic acid, D-polylactic acid, polymandelic acid, copolymer of D,L-lactic acid and glycolic acid, copolymer of D,L-lactic acid and mandelic acid, copolymer of D,L-lactic acid and caprolactone, and copolymer of D,L-lactic acid and 1,4-dioxane-2-one; R is hydrogen atom, or acetyl, benzoyl, decanoyl, palmitoyl, methyl or ethyl; and M is independently Na, K or Li.

[Formula 5]

$$S—O—PAD—COO—Q$$

In Formula 5 above, S is

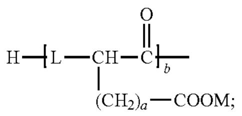

L is —$NR_1$— or —O—, wherein $R_1$ is hydrogen atom or $C_{1-10}$ alkyl; Q is —$CH_3$, —$CH_2CH_3$, —$CH_2CH_2CH_3$, —$CH_2CH_2CH_2CH_3$, or —$CH_2C_6H_5$; a is an integer of from 0 to 4; b is an integer of from 1 to 10; M is Na, K or Li; and PAD is one or more selected from the group consisting of D,L-polylactic acid, D-polylactic acid, polymandelic acid, copolymer of D,L-lactic acid and glycolic acid, copolymer of D,L-lactic acid and mandelic acid, copolymer of D,L-lactic acid and caprolactone, and copolymer of D,L-lactic acid and 1,4-dioxane-2-one.

[Formula 6]

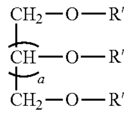

or

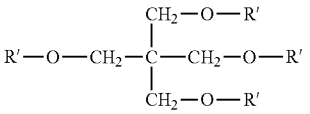

In Formula 6 above, R' is —PAD-O—C(O)—$CH_2CH_2$—C(O)-OM, wherein PAD is selected from the group consisting of D,L-polylactic acid, D-polylactic acid, polymandelic acid, copolymer of D,L-lactic acid and glycolic acid, copolymer of D,L-lactic acid and mandelic acid, copolymer of D,L-lactic acid and caprolactone, and copolymer of D,L-lactic acid and 1,4-dioxane-2-one, M is Na, K or Li; and a is an integer of from 1 to 4.

[Formula 7]

$$YO\text{-}[\text{-}C(O)\text{-}(CHX)_a\text{-}O\text{-}]_m\text{-}C(O)\text{-}R\text{-}C(O)\text{-}[\text{-}O\text{-}(CHX')_b\text{-}C(O)\text{-}]_n\text{-}OZ$$

In Formula 7 above, X and X' are independently hydrogen, $C_{1-10}$ alkyl or $C_{6-20}$ aryl; Y and Z are independently Na, K or Li; m and n are independently an integer of from 0 to 95, with the proviso that 5<m+n<100; a and b are independently an integer of from 1 to 6; and R is —$(CH_2)_k$—, $C_{2-10}$ divalent alkenyl, $C_{6-20}$ divalent aryl or a combination thereof, wherein k is an integer of from 0 to 10.

In an embodiment, the salt of polylactic acid may be a compound of Formula 2 or Formula 3.

In an embodiment, in order to increase the efficiency of intracellular delivery of drug (e.g., mRNA), the nanoparticle of the present invention may further comprise fusogenic lipid.

When mixed with a drug (e.g., mRNA) and the complex of the lipid of the present invention, the fusogenic lipid forms a complex of drug (e.g., mRNA)/the lipid of the present invention/fusogenic lipid by hydrophobic interaction, and the complex comprising the fusogenic lipid is encapsulated within the nanoparticle structure of the amphiphilic block copolymer.

More concretely, the fusogenic lipid may be one or more phospholipid selected from the group consisting of phosphatidylethanolamine (PE), phosphatidylcholine (PC) and phosphatidic acid. The phosphatidylethanolamine (PE), phosphatidylcholine (PC) and phosphatidic acid may be in a form combined with one or two $C_{10-24}$ fatty acids. Cholesterol and tocopherol include analogues, derivatives and metabolites of each of the cholesterol and tocopherol.

Still more concretely, the fusogenic lipid may be one or a combination of two or more selected from the group consisting of dilauroyl phosphatidylethanolamine, dimyristoyl phosphatidylethanolamine, dipalmitoyl phosphatidylethanolamine, distearoyl phosphatidylethanolamine, dioleoyl phosphatidylethanolamine (DOPE), 1,2-dipalmitoleoyl-sn-glycero-3-phosphoethanolamine (DPPE), dilinoleoyl phosphatidylethanolamine, 1-palmitoyl-2-oleoyl phosphatidylethanolamine, 1,2-diphytanoyl-3-sn-phosphatidylethanolamine, 1,2-dipalmitoleoyl-sn-glycero-3-phosphocholine (DPPC), 1,2-dioleoyl-sn-glycero-3-phosphocholine (DOPC), dilauroyl phosphatidylcholine, dimyristoyl phosphatidylcholine, dipalmitoyl phosphatidylcholine, distearoyl phosphatidylcholine, dioleoyl phosphatidylcholine, dilinoleoyl phosphatidylcholine, 1-palmitoyl-2-oleoyl phosphatidylcholine, 1,2-diphytanoyl-3-sn-phosphatidylcholine, dilauroyl phosphatidic acid, dimyristoyl phosphatidic acid, dipalmitoyl phosphatidic acid, distearoyl phosphatidic acid, dioleoyl phosphatidic acid, dilinoleoyl phosphatidic acid. 1-palmitoyl-2-oleoyl phosphatidic acid, 1,2-diphytanoyl-3-sn-phosphatidic acid, cholesterol and tocopherol.

Still more concretely, the fusogenic lipid may be one or more selected from the group consisting of dioleoyl phosphatidylethanolamine (DOPE), 1,2-dipalmitoleoyl-sn-glycero-3-phosphocholine (DPPC), 1,2-dioleoyl-sn-glycero-3-phosphocholine (DOPC), distearoylphosphatidylcholine (DSPC) and 1,2-dipalmitoleoyl-sn-glycero-3-phosphoethanolamine (DPPE).

In an embodiment, the amount of the amphiphilic block copolymer used may be 1 to 500 parts by weight, 1 to 400 parts by weight, 1 to 300 parts by weight, 2 to 500 parts by weight, 2 to 400 parts by weight, 2 to 300 parts by weight, 3 to 500 parts by weight, 3 to 400 parts by weight, 3 to 300 parts by weight, 4 to 500 parts by weight, 4 to 400 parts by weight, or 4 to 300 parts by weight, based on 1 part by weight of the lipid.

In an embodiment, the amount of the salt of polylactic acid used may be 0.1 to 100 parts by weight, 0.1 to 80 parts by weight, 0.1 to 50 parts by weight, 0.1 to 30 parts by weight, 0.1 to 10 parts by weight, 0.1 to 5 parts by weight, 0.5 to 100 parts by weight, 0.5 to 80 parts by weight, 0.5 to 50 parts by weight, 0.5 to 30 parts by weight, 1 to 100 parts by weight, 1 to 80 parts by weight, 1 to 50 parts by weight, 1 to 30 parts by weight, 2 to 100 parts by weight, 2 to 80 parts by weight, 2 to 50 parts by weight, or 2 to 30 parts by weight, based on 1 part by weight of the lipid of the present invention.

In an embodiment, the composition of the present invention may further comprise aqueous solution, water miscible organic solvent, or a combination thereof. The "aqueous solution" may be used for the same meaning as water solution, and may mean, for example, water, sterilized water, buffer solution, injection solution, etc., and it may be a buffer solution further comprising organic acid. The aqueous solution may be, for example, citric acid buffer, PBS buffer, etc., but it is not limited thereto. The "water miscible organic solvent" may be $C_1$ to $C_4$ lower alcohol, acetone, acetonitrile, a water mixture thereof or a mixture thereof, but it is not limited thereto.

In an embodiment, the composition of the present invention may further comprise a stabilizing agent suitable for improving stability of the effective ingredient. The stabilizing agent may further include pH adjusting agent, inorganic salt, saccharide, surfactant, chelating agent, etc., but it is not limited thereto. The "saccharide" may mean monosaccharide, disaccharide, sugar alcohol which is reduced sugar thereof, and polymer of single or mixed polysaccharides, etc., and the polysaccharide may mean tri- or more saccharide. For example, the monosaccharide may be mannose, glucose, arabinose, fructose, galactose, etc.; the disaccharide may be sucrose, trehalose, maltose, lactose, cellobiose, gentiobiose, isomaltose, melibose, etc.; the sugar alcohol may be mannitol, sorbitol, xylitol, erythritol, maltitol, etc.; and the polysaccharide may be raffinose, dextran, starch, hydroxyethyl starch, cyclodextrin, cellulose, hetastarch, oligosaccharide, etc. but it is not limited thereto. The "pH adjusting agent" may be Tris, glycine, histidine, glutamate, succinate, phosphate, acetate, aspartate, or a combination thereof, and the "surfactant" may be sodium lauryl sulfate, dioctyl sodium sulfosuccinate, dioctyl sodium sulfonate, chenodeoxycholic acid, N-lauroylsarcosine sodium salt, lithium dodecyl sulfate, 1-octanesulfonic acid sodium salt, sodium cholate hydrate, sodium deoxycholate, glycodeoxycholic acid sodium salt, benzalkonium chloride, Triton X-100, Triton X-114, lauromacrogol 400, polyoxyl 40 stearate, polysorbate 20, 40, 60, 65 or 80, or a combination thereof, but it is not limited thereto. The "chelating agent" may be citric acid, polyphenolic acid, EDTA, DTPA, EDDHA, or a combination thereof, but it is not limited thereto. The "inorganic salt" means a salt of monovalent or divalent metal and may be NaCl, KCl, $MgCl_2$, $CaCl_2$), $MgSO_4$, $CaSO_4$, $CaCO_3$, $MgCO_3$, etc., but it is not limited thereto.

The composition of the present invention may be suitable for delivery to specific organs. The organs include lung, heart, brain, liver, gallbladder, kidney, spleen, pancreas, eye, nose, ear, thyroid, uterus, ovaries, testes, stomach, small intestine, large intestine, rectum, etc., but are not limited thereto. More concretely, the composition of the present invention may be suitable for delivery to lung or nasal administration.

The present invention will be explained below in more detail with reference to the following Examples. However, the Examples are only to illustrate the invention, and the scope of the present invention is not limited thereby in any manner.

EXAMPLES

Synthesis of Lipid of Formula 1 (2OA-PAMAM)

(1) Preparation of dimethyl 3,3'-((2-((tert-butoxycarbonyl)amino)ethyl)azanediyl) dipropionate (Boc-2MeO-PAMAM)

[Boc-2MeO-PAMAM]

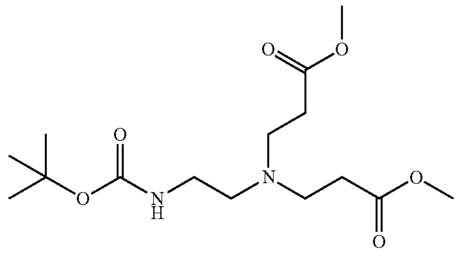 [SMILES: COC(=O)CCN(CCNC(=O)OC(C)(C)C)CCC(=O)OC]

In a 100 mL three-neck round bottom flask (RBF) (reactor 1), N-tert-butoxycarbonyl (N-Boc) ethylenediamine (4 g, 24.97 mmol, 1 eq) and methanol (MeOH) (30 mL) were added and cooled to 0° C., and then methyl acrylate (8.60 g, 99.87 mmol, 4 eq) was added dropwise to reactor 1. Then, the mixture was stirred at room temperature for 24 hours, and concentrated under vacuum [yield: 8.25 g (99%)].

(2) Preparation of tert-butyl (2-(bis(3-(((Z)-octadec-9-en-1-yl)amino)-3-oxopropyl)amino)ethyl)carbamate) (Boc-2OA-PAMAM)

[Boc-2OA-PAMAM]

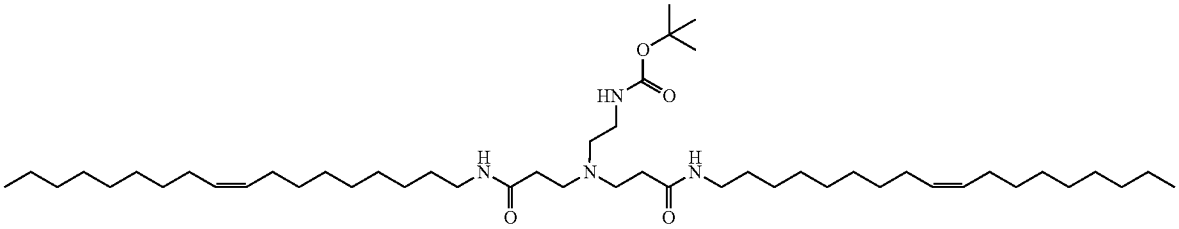 [SMILES: CCCCCCCC/C=C\CCCCCCCCNC(=O)CCN(CCNC(=O)OC(C)(C)C)CCC(=O)NCCCCCCCC/C=C\CCCCCCCC]

In a 100 mL three-neck round bottom flask (RBF) (reactor 1), Boc-2MeO-PAMAM (4 g, 12.04 mmol, 1 eq) prepared in the above step (1) and oleylamine (9.66 g, 36.12 mmol, 3 eq) were added, and reacted with stirring at 80° C. for 6 days. Then, the product was purified using a silica gel column by changing the developing solvent from 100% ethyl acetate (EA) to EA:MeOH (20:1) [yield: 4.6 g (48%)].

(3) Preparation of 3,3'-((2-aminoethyl)azanediyl)bis (N-((Z)-octadec-9-en-1-yl)propanamide)) (2OA-PAMAM)

[2OA-PAMAM]

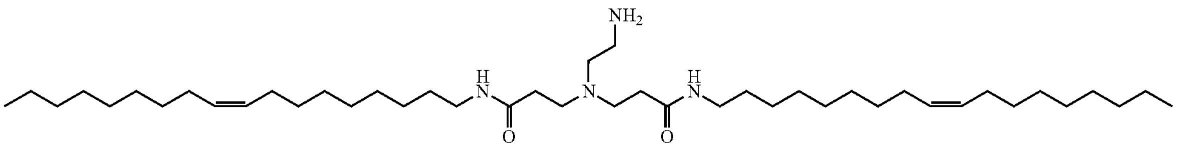 [SMILES: CCCCCCCC/C=C\CCCCCCCCNC(=O)CCN(CCN)CCC(=O)NCCCCCCCC/C=C\CCCCCCCC]

In a 100 mL three-neck round bottom flask (RBF) (reactor 1), Boc-2OA-PAMAM (2.2 g, 2.74 mmol, 1 eq) prepared in in the above step (2) and dichloromethane (MC) (18 mL) were added and cooled to 0° C. Trifluoroacetic acid (2 mL) was added dropwise to reactor 1 and the mixture was stirred at 25° C. for 12 hours. Then, the mixture was diluted with MC (200 mL) and extracted three times with saturated $NaHCO_3$ aqueous solution (200 mL). The organic layer was taken, moisture was removed with $Na_2SO_4$, and the solvent was evaporated. Then, the final product was purified using a silica gel column using EA:MeOH (1:2) as a developing solvent. NMR data of the obtained final product are shown in FIG. 1 [yield: 0.79 g (41%)].

Test of Delivery to Cell

1. Drug Delivery Test (1) Preparation of Solutions for Each Component

The components shown in Table 1 below were dissolved in each dilution solvent to prepare their solutions at the concentrations shown in Table 1 below. When dissolving, a bath sonicator was used for about 5-10 minutes, and the solutions were used after visually confirming that there were no undissolved particles. For dioleoyl phosphatidylethanolamine (DOPE) and cholesterol, the solutions were incubated in an oven at 65° C. for about 5 minutes and used in the test after visually confirming that there was no precipitation.

TABLE 1

| No. | Components | Dilution solvents | Concentration for use |
|---|---|---|---|
| 1 | mRNA | RNAse free water | 1 mg/mL |
| 2 | 2OA-PAMAM | Ethanol 100% | 10-20 mg/mL |
| 3 | mPEG-PLA(2K-4K) | Ethanol 95% | 50-100 mg/mL |
| 4 | DOPE | Ethanol 100% | 10-20 mg/mL |
| 5 | Cholesterol | Ethanol 100% | 10-20 mg/mL |

[mPEG-PLA(2K-4K): Copolymer of monomethoxypolyethylene glycol (mPEG) block with a number average molecular weight of 2,000 and polylactic acid (PLA) block with a number average molecular weight of 4,000]

(2) Preparation of Composition

The required amounts of the components were mixed in order to meet the N/P ratio (amine group of lipid component/phosphate group of mRNA) of 20 and 2OA-PAMAM:mPEG-PLA(2K-4K):DOPE:cholesterol=5:5:1:4. Ethanol was added to the ethanol layer so that the molecular total of all components was 6.25-12.5 mM, and the aqueous phase and ethanol phase were mixed maintaining a ratio of 3:1. After mixing, the total amount was diluted 20 times with PBS to lower the total ethanol content, and then concentrated using Amicon-Ultra tube filter (Merk Millipore, UFC505096 or UFC805024, pore size: 50K, volume: 0.5 mL or 4 mL). The buffer used in the aqueous phase was 20 mM sodium acetate buffer (pH 4.6) (This was prepared by diluting 3M sodium acetate buffer to 20 mM and titrating it to pH 4.6 using 1M HCl). The more concrete procedure of composition preparation is as follows:

1) Two autoclaved tubes were prepared (tubes (A) and (B)).
2) In tube (A), 2OA-PAMAM, DOPE, cholesterol, and mPEG-PLA (2K-4K) in molar quantities calculated according to the experimental conditions were sequentially added and mixed by vortexing.
3) In the ethanol phase, when necessary, ethanol was added so that the molecular total of all components was within 12.5 mM (In the case of mPEG-PLA, since at least 3% of water was required for complete dissolution, if the solution became cloudy after adding ethanol, the minimum amount of water was added for dissolution).

4) In tube (B), mRNA and 20 mM sodium acetate buffer (pH 4.6) were mixed. At that time, the ratio was calculated and added so that the aqueous phase was total three times the amount of the ethanol phase.

5) The solution in tube (B) was transferred to tube (A) and mixed. At that time, the mixing was performed as quickly as possible to make a uniform formulation, and then vortexing was performed for mixing.

6) The prepared formulation was added to PBS in total volume of 20 times for dilution to make the ethanol content 5% or less.

7) After dilution, the formulation was centrifuged using Amicon Ultra Centrifugal Filter Units (50K) until it was concentrated to the desired volume depending on the purpose.

(3) Administration of Composition

The formulation prepared according to the above method was prepared at 2 μg/200 μL based on mRNA, and administered intravenously to mice. After 4 hours, luciferin dissolved in sterile water was prepared at 15 μg/μL and administered intraperitoneally so that 3 mg of luciferin was administered per 20 g mouse. After 15 minutes from the intraperitoneal administration of luciferin, protein expression results were measured using a luminescence measurement imaging system and are shown in FIG. 2.

As confirmed in FIG. 2 and Table 2, the drug-containing nanoparticle formulation prepared using the lipid according to the present invention had very excellent delivery efficiency when administered intravenously.

TABLE 2

| | Average RLU |
|---|---|
| Example | 2.3.E+04 |
| Comparative Example | 3.7.E+03 |

2. Intranasal Administration Test

The formulation prepared in Test 1 above was prepared at 2 μg/200 μL and administered intranasally to mice. Then, the results were measured using a luminescence measurement imaging system and are shown in FIG. 3.

Meanwhile, as comparative examples, for SM102 [Heptadecan-9-yl 8-((2-hydroxyethyl)(6-oxo-6-(undecyloxy)hexyl)amino)octanoate], SSOP [((((((disulfanediylbis(ethane-2, 1-diyl))bis(piperidine-1,4-diyl))bis(ethane-2,1-diyl))bis(oxy))bis(2-oxoethane-2,1-diyl))bis(4,1-phenylene) dioleate] and 20T [N,N'-((ethane-1,2-diylbis(azanediyl))bis(ethane-2,1-diyl))dioleamide], the formulations were prepared in the same composition and the same ratio using the same method as in the example. and administered intranasally in the same manner. The results are shown in FIG. 3.

The invention claimed is:

1. A lipid having the following structure

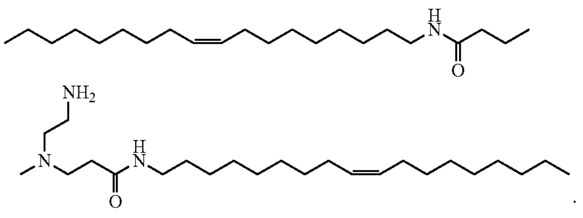

2. A method for preparing the lipid according to claim 1, comprising the steps of:

(1) reacting a compound of the following formula a with methyl acrylate to obtain a compound of the following formula b;

(2) reacting a compound of the following formula b with a compound of the following formula c-1 to obtain a compound of the following formula d-1; and (3) deprotecting the compound of formula d-1:

[Formula a]

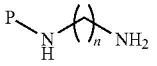

[Formula b]

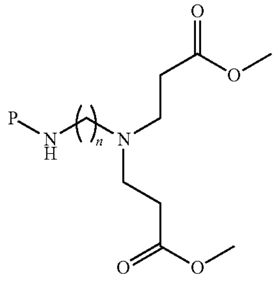

[Formula c-1]

$R_1$—$NH_2$

[Formula d-1]

[Formula d-1]

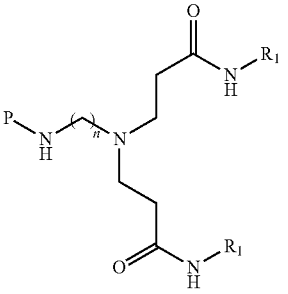

wherein,

P is a protecting group, n is 2, and $R_1$ is $—(CH_2)_8CH═CH(CH_2)_7CH_3$.

3. A composition for drug delivery comprising the lipid of claim 1.

4. Drug-containing nanoparticle comprising: a drug as effective ingredient; an amphiphilic block copolymer; and the lipid of claim 1, wherein the drug and the lipid form a complex, and the complex is encapsulated within nanoparticle structure formed by the amphiphilic block copolymer.

5. The drug-containing nanoparticle according to claim 4, wherein the drug-containing nanoparticle further comprises a salt of polylactic acid, and the complex is encapsulated within a nanoparticle structure formed by the amphiphilic block copolymer and the salt of a polylactic acid.

6. A composition for drug delivery comprising the drug-containing nanoparticle of claim 4.

7. A composition for drug delivery comprising the drug-containing nanoparticle of claim 5.

* * * * *